US008388661B2

(12) United States Patent
Schlaepfer et al.

(10) Patent No.: US 8,388,661 B2
(45) Date of Patent: Mar. 5, 2013

(54) ROD CONNECTOR FOR ATTACHING A BONE ANCHOR TO A SUPPORT ROD AND IMPLANTATION INSTRUMENT THEREFOR (75) Inventors: Fridolin J. Schlaepfer, Hoelstein (CH); Peter Senn, Waldenburg (CH)

(73) Assignee: Synthes USA, LLC, West Chester, PA (US)

( * ) Notice: Subject to any disclaimer, the term of this patent is extended or adjusted under 35 U.S.C. 154(b) by 745 days.

(21) Appl. No.: 12/063,807

(22) PCT Filed: Aug. 18, 2005

(86) PCT No.: PCT/EP2005/008959
§ 371 (c)(1),
(2), (4) Date: Jul. 21, 2010

(87) PCT Pub. No.: WO2007/019873
PCT Pub. Date: Feb. 22, 2007

(65) Prior Publication Data
US 2010/0292735 A1    Nov. 18, 2010

(51) Int. Cl.
*A61B 17/70* (2006.01)
(52) U.S. Cl. .................... 606/278; 606/86 A
(58) Field of Classification Search .......... 606/250–253, 606/276–278, 86 A, 99, 279, 259, 260, 86 B, 606/100
See application file for complete search history.

(56) References Cited

U.S. PATENT DOCUMENTS 6,648,888 B1    11/2003  Shluzas
7,666,189 B2 *   2/2010  Gerber et al. ................. 606/104
7,909,835 B2 *   3/2011  Oribe et al. ................... 606/104
2003/0225408 A1* 12/2003 Nichols et al. ................ 606/61
2004/0049191 A1*  3/2004  Markworth et al. ........... 606/61
2004/0138662 A1   7/2004  Landry et al.
2004/0172022 A1*  9/2004  Landry et al. ................. 606/61
2004/0249378 A1* 12/2004  Saint Martin et al. ......... 606/61
2004/0267275 A1* 12/2004  Cournoyer et al. ............ 606/99
2005/0131408 A1*  6/2005  Sicvol et al. .................. 606/61
2006/0106382 A1*  5/2006  Gournay et al. ............... 606/61

OTHER PUBLICATIONS

International Search Report, completed Mar. 7, 2006 for International Application No. PCT/EP2005/008959, filed Aug. 18, 2005.

* cited by examiner

*Primary Examiner* — Ellen C Hammond
*Assistant Examiner* — Atiya Mahmud
(74) *Attorney, Agent, or Firm* — Stradley Ronon Stevens & Young, LLP (57) ABSTRACT

A rod connector (1) is provided for use in attaching a bone anchor (5) to a support rod (3). The connector (1) comprises a first portion (2) defining a clamping means (6) with an aperture (7) in which the support rod (3) can be located, and a second portion (4) defining a first bore (9) in which a stem of the anchor (5) can be inserted. The connector (1) also comprises a means (12) defining a pivot axis (14) enabling it to be connected to an implantation instrument (11) and orientated in a first position wherein the clamping means (6) can be located around a support rod (3) and then rotated around the rod (3) into a second position relative thereto wherein said bone anchor (5) can be inserted into the bore (9) and then secured to an adjacent bone. In addition, the connector defines first and second retaining means (15, 16) enabling it to be retained by the instrument (11) respectively in said first position and in its second position.

12 Claims, 9 Drawing Sheets

ROD CONNECTOR FOR ATTACHING A BONE ANCHOR TO A SUPPORT ROD AND IMPLANTATION INSTRUMENT THEREFOR

The present invention relates to a rod connector for use in the stabilization of spinal instability, to an assembly comprising the rod connector for use in the implantation of the latter or as a surgical instrument, and to a method of attaching a bone anchor to a support rod using the rod connector.

Spinal instability can occur for a variety of reasons, for example deformity, skeletal instability, tumours, fractures and degenerative diseases. Such instability is conventionally treated by the implantation of one or a pair of support rods that are each attached to several vertebrae via connectors that are themselves attached to the vertebrae by one or more bone anchors such as bone screws.

Conventionally, three types of system are used in the correction and stabilization of spinal deformities from the anterior, namely single support rod, single screw systems; single support rod, double screw systems; and double support rod, double screw systems. Single rod, single screw systems are easy to handle and can potentially be implanted with a minimal surgical opening, for example using an endoscopic approach. However, such systems have the disadvantage that the single screw connection increases the risk that the screws may pull out and if implanted in the lumbar spinal region, there is no rotational stability in the sagittal plane. Single and double rod and double screw systems, in contrast, have a very low risk of bone screw pull-out and provide rotational stability in the sagittal plane when implanted in the lumbar spinal region. However, both of these systems have the disadvantages that two bone screws must be inserted per vertebra, with the increased risk of spinal cord damage by misaligned screws; that there is a reduced potential for implantation via a minimal opening and by using an endoscopic approach, particularly with the double rod system; and that handling and implantation of the system is more difficult because two bone screws per vertebra must be inserted and, in the case of the double rod system two support rods must be inserted in addition.

When dealing with tumours, fractures and degenerative diseases from the anterior, systems are employed that require two bone screws per vertebra with either a single support rod or double support rods. The number of rods does not affect the pull-out strength and rotational stability in the sagittal plane and the risk of damage to the spinal cord is independent of the number of rods. However, the number of rods does influence the handling, approach and access to the intervertebral space. Single rod systems give good access to the intervertebral space, unlike double rod systems, and both systems have the same disadvantages as the systems used for treating spinal deformities in that in both cases there is a reduced potential for implantation via a minimal opening and by using an endoscopic approach and handling and implantation of the systems is more difficult because two bone screws per vertebra must be inserted and, in the case of the double rod system, two support rods must be inserted in addition.

It is an object of the present invention to provide a rod connector, an assembly incorporating same and a method of attaching a bone anchor to a support rod using the rod connector that overcomes or substantially mitigates the disadvantages of conventional systems and methods as described above. In particular, the invention allows for the selective use of one or two bone screws, is easy to handle and requires only a minimal surgical opening allowing for an endoscopic approach. In addition, the invention allows the rod connector to be added on to existing single rod systems, such as a polyaxial screw system, using an endoscopic approach.

According to a first aspect of the present invention there is provided a rod connector for use in attaching a bone anchor to a support rod comprising a first portion adapted for connection to said support rod and defining a clamping means with a aperture in which said support rod can be located, and a second portion adapted for connection to a bone anchor and defining a first bore therethrough in which a stem of the anchor can be inserted, characterised in that the connector comprises a means defining a pivot axis enabling it to be connected to an implantation instrument and orientated in a first position wherein the clamping means can be located around a support rod and then rotated around the rod into a second position relative thereto wherein said bone anchor can be inserted into the bore and thence secured to an adjacent bone; and in that the connector defines first and second retaining means enabling the connector to be retained by the instrument respectively in said first position during location around said support rod and in its second position during connection of said bone anchor.

Preferably, the first and second retaining means respectively comprise first and second sockets in which a locking bolt can be inserted.

Preferably also, the first and second sockets have longitudinal axes that are orientated at right angles to one another.

Preferably also, the second socket and the first bore have longitudinal axes that are parallel to one another.

Preferably also, the longitudinal axes of the first and second sockets intersect at a point coincident with the pivot axis.

Preferably also, the longitudinal axis of the first bore is angled at an acute angle to a plane coincident with the longitudinal axis of the first pivot means that is itself parallel to a plane coincident with the longitudinal axis of the central part of a support rod secured with in the clamping means. Advantageously, the acute angle is of the order of 7°.

Preferably also, the means comprises a third socket in which a spigot can be located around which the connector can pivot.

Preferably also, the first portion of the connector is provided with a setscrew enabling the connector to be clamped to a support rod located within the clamping means.

Preferably also, the clamping means comprises a clamping hook with a bight in which the support rod can be located.

Preferably also, the second portion comprises a second bore therethrough to enable a second bone anchor to be secured to said bone.

According to a second aspect of the present invention there is provided an assembly of a rod connector in accordance with the first aspect of the present invention and an instrument for use in the implantation of the rod connector into a patient, characterised in that the instrument comprises a holder with a pivot means that can engage with the means of the rod connector such that the connector can be pivotally mounted on the holder and rotate around the pivot axis between said first position and said second position relative both to a support rod located in the aperture of the clamping means and to the holder; and a locking means that cooperates with the retaining means defined by the connector to retain the connector relative to the holder either in said first position or in said second position, as desired.

Preferably, the holder comprises a hollow tube and the connector is dimensioned relative thereto such that when the connector is pivotally mounted on the holder and retained in its second position, the longitudinal axis of the hollow tube aligns with the longitudinal axis of the first bore of the connector.

Preferably also, the instrument additionally comprises a guide that retains the connector in said pivotally mounted position on the pivot means of the holder.

Preferably also, the guide comprises a sleeve with a projecting lug that is located around the holder and that can slide relative to the holder in order to position the lug either in an active position wherein it retains the connector in the pivotally mounted position on the holder or in a retracted position wherein the engaging means and pivot means of the connector and the holder respectively can be disengaged from one another.

Preferably also, the locking means comprises a bolt that can be moved relative to the holder into either the first socket or the second socket of the connector to retain the connector respectively in its first or its second position relative to the holder and that can be retracted to enable the connector to rotate relative to the holder.

Preferably also, the guide is attached to the locking means and the linear movement of the locking means relative to the holder additionally moves the lug into and out of said active and retracted positions.

Preferably also, the holder is provided with a clamping bracket for securement of the instrument in a fixed position during use.

Preferably also, a screwdriver and/or an awl are provided for use with the instrument, the screwdriver and/or the awl being dimensioned such that it can be inserted down the hollow tube of the holder.

According to a third aspect of the present invention there is provided a surgical instrument comprising a permanent assembly of a rod connector and an insertion instrument, wherein the rod connector comprises a first portion adapted for connection to a support rod and defining a clamping means with an aperture in which the support rod can be located; characterised in that the connector comprises a means defining a pivot axis enabling it to be orientated in a first position with respect to said implantation instrument wherein the clamping means can be located around a support rod and then rotated around the pivot axis into a second position; and first and second retaining means enabling the connector to be retained by the implantation instrument respectively in said first position during location around said support rod and thence in said second position; and in that the insertion instrument comprises a holder with a pivot means that can engage with the means of the rod connector such that the connector can rotate around the pivot axis between said first position and said second position relative to a support rod located in the aperture of the clamping means; and a locking means that cooperates with the first and second retaining means defined by the connector to retain the connector relative to the holder either in said first position or in said second position, as desired.

It will be appreciated that when the connector is firmly attached to the rod in the first position by locking means such as a set screw, the rod can be rotated from the first position, A, into the second position, B, by rotating the connector from the first position into the second position. This type of manoeuvre is used for the correction of scoliotic deformities.

According to a fourth aspect of the present invention there is provided an assembly comprising a rod connector for use in attaching a bone anchor to a support rod and an implantation instrument for use in the implantation of the rod connector into a patient; the rod connector comprising a first portion adapted for connection to said support rod and defining a clamping means with a aperture in which the support rod can be located, and a second portion adapted for connection to said bone anchor and defining a first bore therethrough in which a stem of the anchor can be inserted, characterised in that the rod connector and the implantation instrument are interconnected through complementary means with a common pivot axis.

According to a fifth aspect of the present invention there is provided a method of attaching a bone anchor to a support rod comprising the steps of providing a rod connector defining a clamping means with an aperture in which the support rod can be located, and a second portion adapted for connection to said bone anchor and defining a first bore therethrough in which a stem of the anchor can be inserted; providing an implantation instrument comprising a holder with a pivot means that can engage with the means of the rod connector such that the connector can be pivotally mounted on the holder and rotate around the pivot axis, and locking means that cooperates with the connector to retain the connector relative to the holder either in a first position wherein the clamping means can be located around a support rod or in a second position wherein a bone anchor can be inserted into the bore; connecting the means of the rod connector to the pivot means of the implantation instrument to form an assembly of the rod connector and said implantation instrument; and deploying the locking means to lock the rod connector in said first position relative to the implantation instrument; inserting the rod connector into a patient using the implantation instrument; locating the clamping means around a support rod that has been previously implanted into the patient; loosening the locking means sufficiently to permit the rod connector rotate about the pivot axis; manipulating the implantation instrument in order to rotate the rod connector about the pivot axis from said first position into said second position; deploying the locking means to lock the rod connector in said second position relative to the implantation instrument and to the support rod; securing the rod connector to a bone of the patient using a bone anchor inserted through the first bore of the rod connector; and disassembling the means of the rod connector from the pivot means of the implantation instrument in order to enable the implantation instrument to be withdrawn from the patient leaving the rod connector implanted in the patient.

The various aspects of present invention will now be described by way of example with reference to the accompanying drawings, in which.

Figure 1:
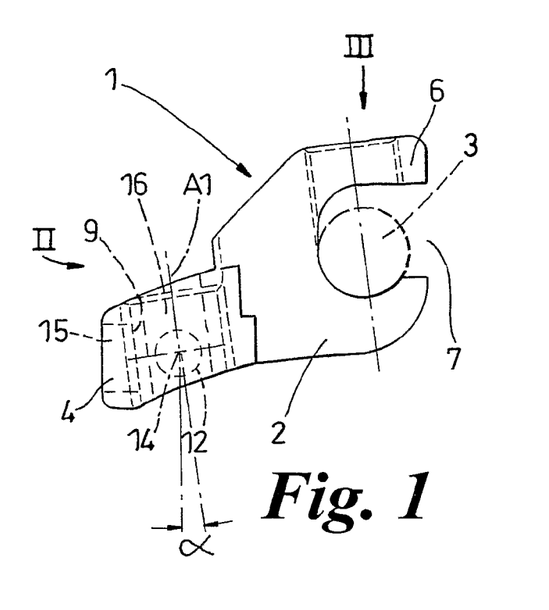
FIG. 1 is a side view of a rod connector in accordance with the first aspect of the present invention.
Figure 2:
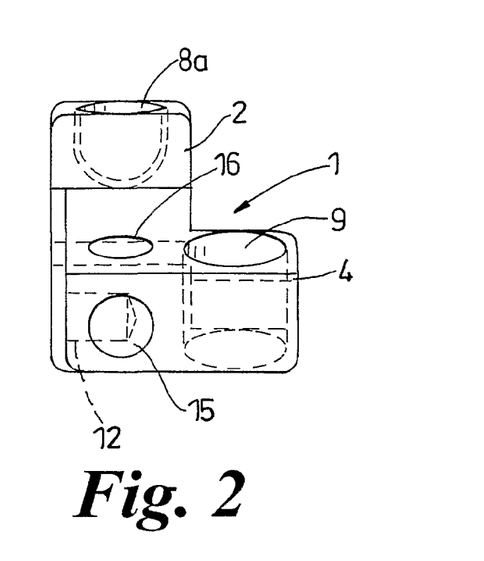
FIGS. 2 and 3 are respectively end and plan views of the connector in the direction of arrows II and III in FIG. 1.
Figure 3:
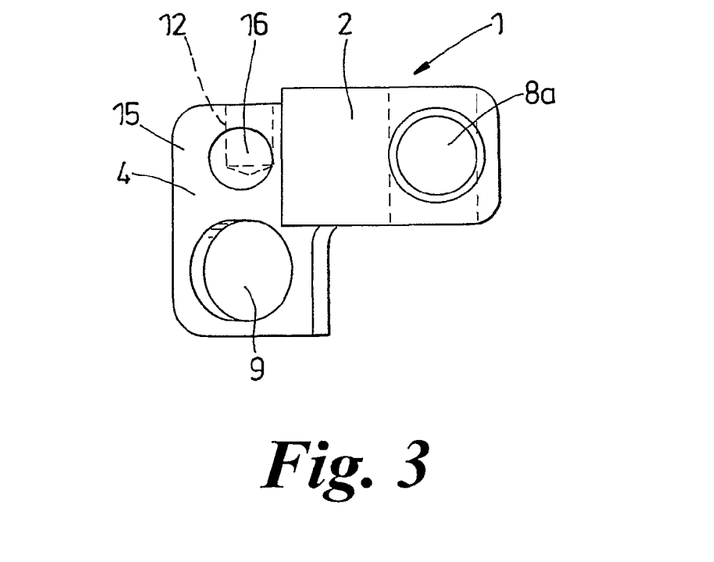
Figure 11:
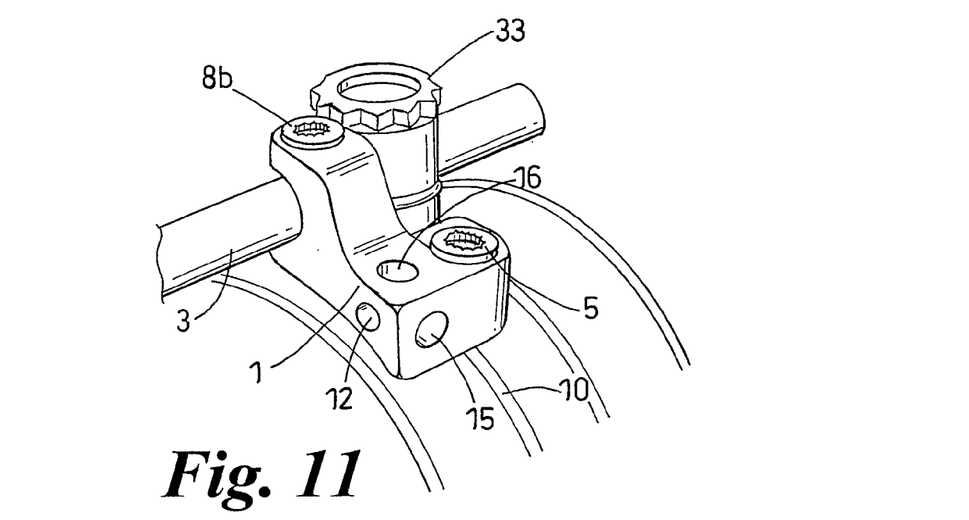
FIG. 11 is a perspective view of a rod connector as shown in FIGS. 1 to 3 after implantation and securement to a support rod.

With reference to FIGS. 1 to 3, a rod connector 1 for use in attaching a bone anchor to a support rod comprises a first portion 2 adapted for connection to a support rod 3 (as shown in dashed lines in FIG. 2 and after implantation in FIG. 11) and a second portion 4 adapted for connection to a bone anchor 5, such as a bone screw (again as shown in FIG. 11). The first portion 2 defines a clamping means in the form of a clamping hook 6 defining an aperture in the form of a bight 7 in which the support rod 3 can be located. It will be appreciated that the bight 7 can be of a sufficient size and shape to accommodate particular sizes of support rods 3 for use in different patients and for particular purposes. The clamping hook 6 is also provided with a bore 8a for a setscrew 8b (not shown in FIGS. 1 to 3) enabling the connector 1 to be clamped to the support rod 3 after its location within the bight 7.

The second portion 4 is provided with a tapped bore 9 therethrough in which the threaded stem of the anchor 5 can be inserted and secured to a vertebra 10 (see FIG. 11). Such an anchor 5 can be of conventional design with a thread adapted to compress cancellous bone tissue.

In order that the connector 1 is easy to handle and requires only a minimal surgical opening for implantation, it is provided with features, as will now be described, that adapt it for implantation by means of a specially designed instrument 11, that is described below and with which it can form an assembly that can also be used as an instrument to perform certain functions.

Between the bore 9 and the clamping hook 6 the connector is provided with a first pivot means that engages with a second pivot means provided on the instrument 11 such that the connector 1 can be pivotally mounted on the instrument 11. In this example, the first pivot means comprises a pivot socket 12 enabling the connector 1 to be mounted on a spigot 13 comprising the second pivot means (see FIG. 5) for rotation around a pivot axis 14. During implantation, the connector 1 is rotated about the spigot 13 from a first position into a second position so that the bore 9 moves from a first orientation through 90° into a second orientation wherein an anchor 5 can be located therein and secured to a vertebra 10 (see FIG. 11). In order to enable the connector 1 to follow the curvature of the exterior of the vertebra 10, the bore 9 is positioned through the second portion 4 such that its longitudinal axis A1 is angled at an angle α to a plane coincident with the pivot axis 14 of the pivot socket 12 that is parallel to a plane coincident with the longitudinal axis of that part of the support rod 3 located fully in the bight 8, as shown in FIG. 2. This angle α can be varied as appropriate but is typically of the order of 7°.

In addition, the connector 1 is provided with first and second retaining means in the form of sockets 15 and 16 that enable the connector 1 to be retained respectively in the first position during its location around the support rod 2 and in its second position during connection of the bone anchor 5. The sockets 15 and 16 are located on adjoining faces of the second portion 4 of the connector 1 adjacent the bore 9 and they have longitudinal axes that are orientated at right angles to one another. In addition, the longitudinal axes of the sockets 15 and 16 intersect at a point coincident with the longitudinal axis of the pivot socket 12.

Figure 4:
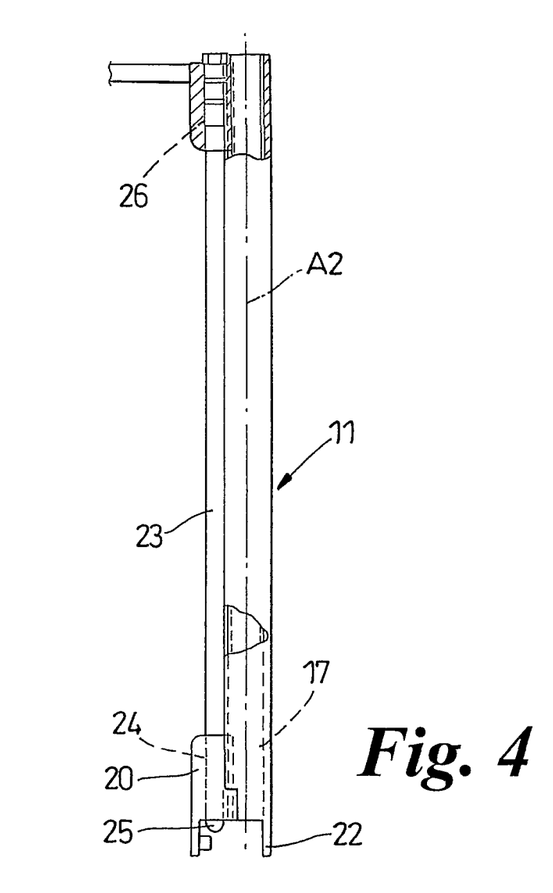
FIG. 4 is a side view of an instrument forming part of an assembly according to the second aspect of the invention for use in the implantation of the rod connector shown in FIGS. 1 to 3 but to a smaller scale than these figures.
Figure 5:
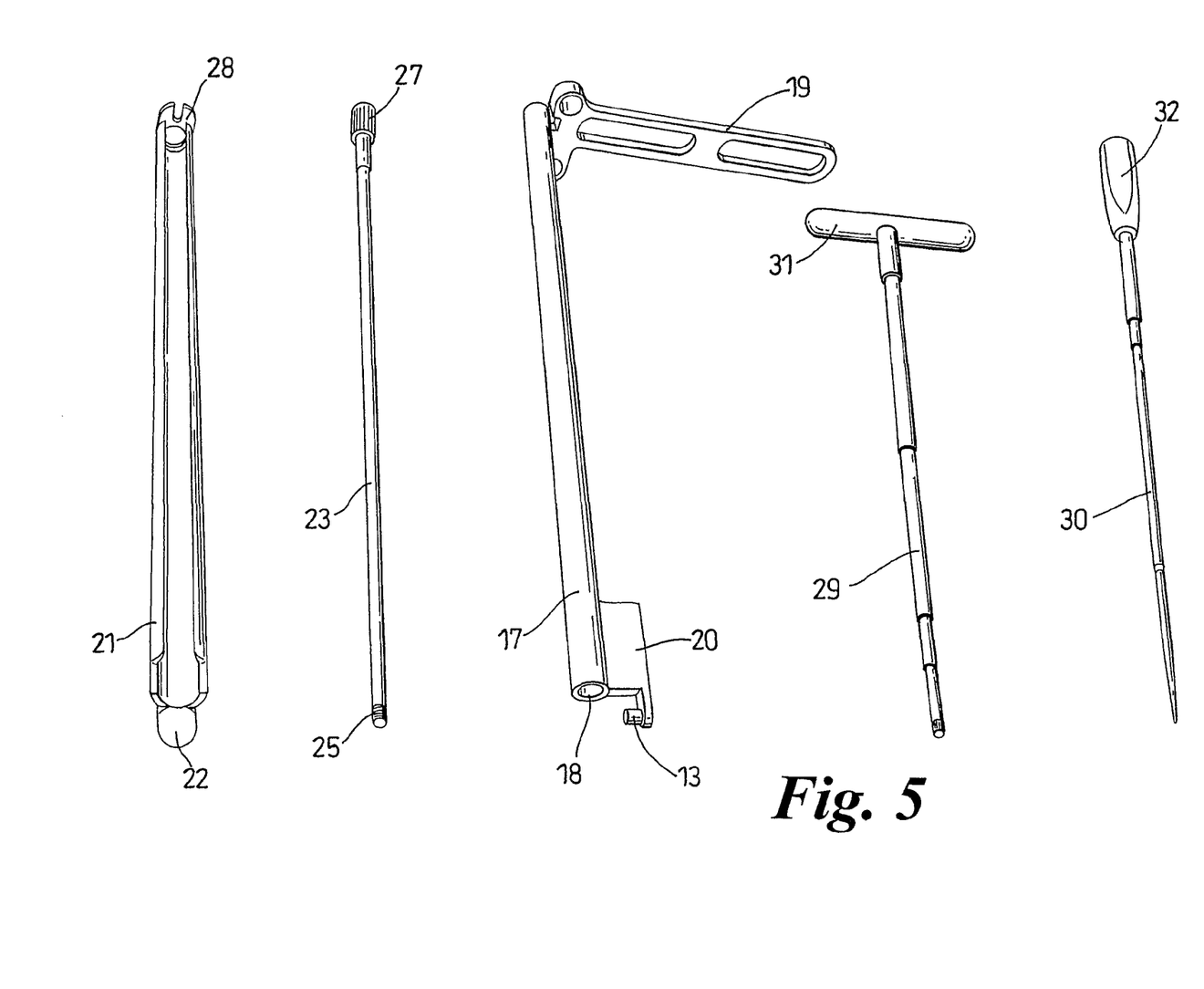
FIG. 5 is an exploded view of the instrument together with a screwdriver and an awl for use therewith.
Figure 6:
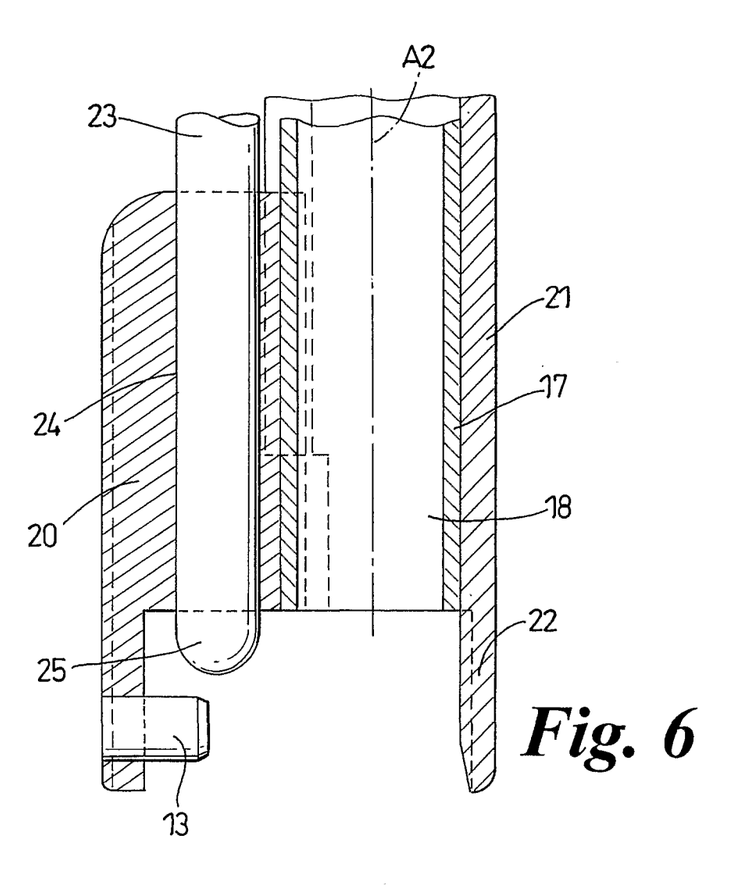
FIG. 6 is a cross-sectional view, to an enlarged scale, of an end of the instrument designed for connection to the rod connector.

The instrument 11 used during implantation of the connector 1 will now be described with reference to FIGS. 4, 5 and 6.

The instrument 11 is at least partially cannulated and comprises a holder 17 in the form of a linear tube 18 with a longitudinal axis A2. At one end of the holder 17 is a clamping bracket 19 to permit the instrument to be clamped in position to a stand (not shown) located adjacent the patient during an implantation operation. The other end of the holder 18 is provided with a lateral extension 20 that defines the second pivot means in the form of the spigot 13, as mentioned above, which projects transversely relative to the tube 18 at a location beyond its end. The spigot 13 can engage within the pivot socket 12 of the connector enabling the connector 1 to pivot around this end of the instrument 11. In order to hold the connector 1 on the spigot 13 but still enable it to pivot, the instrument 11 comprises a guide 21 in the form of a sleeve which can slide up and down the length of the tube 18. At the end adjacent the spigot 13, the guide 21 is provided with a projecting lug 22. The connector 1 can be located on the spigot 13 when the guide 21 is retracted and then by sliding the guide 21 towards the connector, the lug 22 overlies the end of the connector 1 opposite the pivot socket 12 thereby preventing the connector 1 from moving off the spigot 13.

In order the retain the connector 1 in its first and second positions, the instrument 11 is also provided with a locking means 23 that can be moved relative to the tube 18 into one or other of the sockets 15 and 16 of the connector 1. The locking means 23 runs along the exterior of the tube 18 and passes through a bore 24 in the lateral extension 20 in order that its end 25 can be extended and retracted adjacent the spigot 13 into and out of the sockets 15 and 16 of the connector 1 in the manner of a bolt. The other end of the locking means 23 adjacent the clamping bracket 19 is tapped and screwed through a threaded bore 26 in the holder 17 in order that fine adjustments of its position relative to the tube 18 can be made. To facilitate this, this end of the locking means 23 is provided with a knurled knob 27.

The locking means bolt 23 also controls movement of the guide 21 relative to the tube 18. To this end, the guide 21 is provided with a collar 28 that fits around a waisted portion of the bolt 23 between the end of the bore 26 and the knob 27. The collar 28 allows rotational movement of the locking means 23 but ensures that the guide 21 moves linearly with the locking means 23 as it also moves linearly relative to the tube 18. Screwing of the locking means 23 into and out of the bore 26 thereby moves the guide 21 relative to the tube 18 allowing the lug 22 to be extended or retracted with respect to the connector 1.

It should be appreciated that the connector 1 and the instrument 11 are designed to form an assembly for use in the implantation of the connector 1 into a patient. To this end, as will now be described, when the connector 1 is pivotally mounted on the spigot 13 in its second position wherein the bolt 25 engages in the socket 16, the longitudinal axis of the tube 18 aligns with the longitudinal axis of the bore 9 of the connector 1. The stem of a bone anchor 5 can, therefore, be inserted into the bore 9 for connection to a vertebra 10 via the tube 18 and a screwdriver 29 and an awl 30 are provided for use with the instrument 11. Both the screwdriver 29 and the awl 30 are dimensioned such that they can be inserted down the tube 18 of the holder 17 and operated via handles 31 and 32 respectively from the end of the instrument 11 adjacent the clamping bracket 19.

The use of an assembly comprising the connector 1 and the instrument 11 in an operation to implant a rod connector 1 into a patient by connection to an existing support rod 3 will now be described with reference to the sequence of FIGS. 7 to 10.

Figure 7:
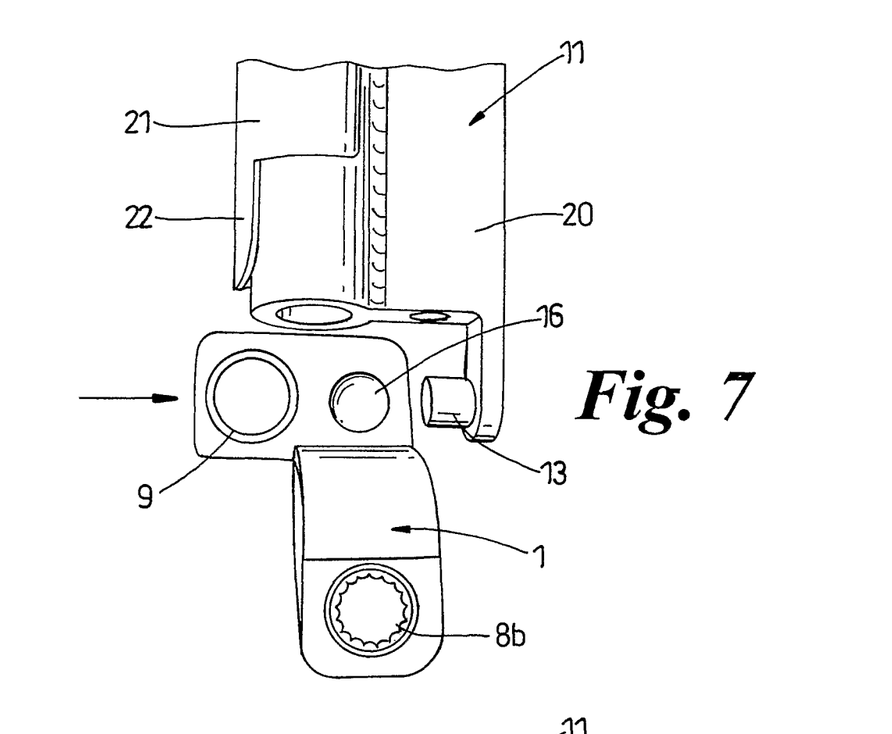
FIGS. 7 to 10 is a sequence of drawings showing the assembly of a rod connector as shown in FIGS. 1 to 3 with the end of the instrument shown in FIG. 6 as deployed in an operation to implant the rod connector.
Figure 8:
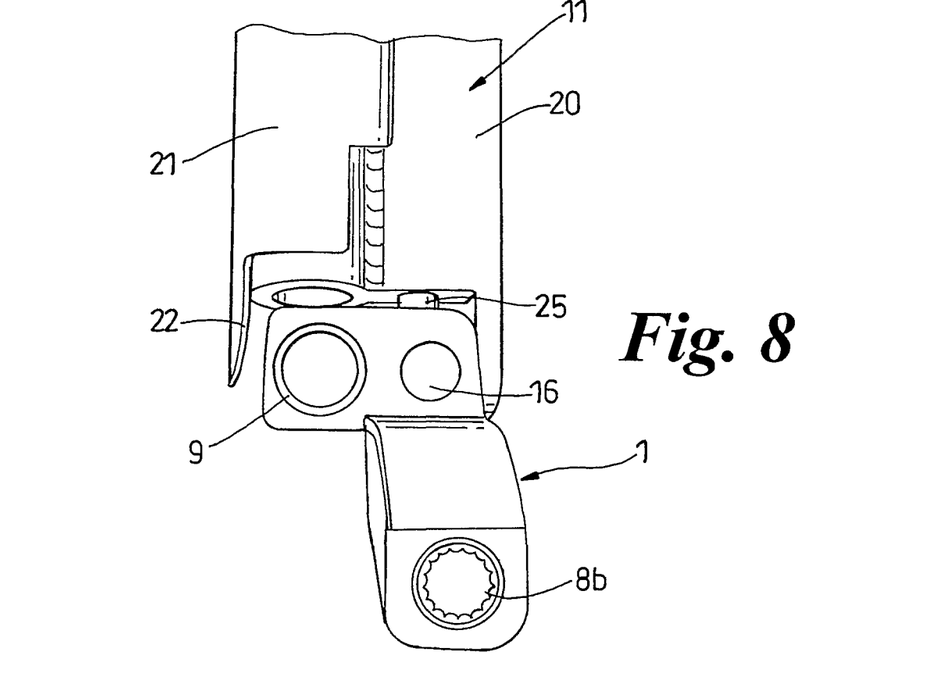

Initially and external to the patient, the connector 1 is attached to the instrument 11 by engaging the pivot socket 12 over the spigot 13 (see FIG. 7). The connector 1 is orientated so that the bore 9 is substantially transverse to the longitudinal axis A2 of the tube 18 and in order to hold the connector 1 in this position the guide 21 is projected by turning the knob 27 of the locking means 23 so that the lug 22 overlies the end of the connector 1 opposite to the pivot socket 12. Further turning of the knob 27 lowers the bolt 25 so that it engages in the socket 15. The connector 1 is now firmly secured to the instrument 11 in a position wherein it neither be moved off the spigot 13 nor pivoted around it (see FIG. 8).

Figure 9:
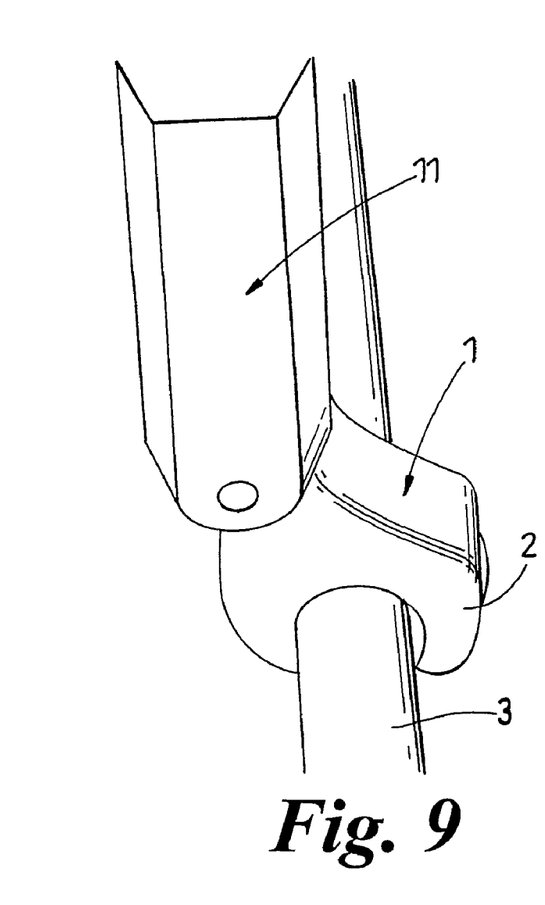
Figure 10:
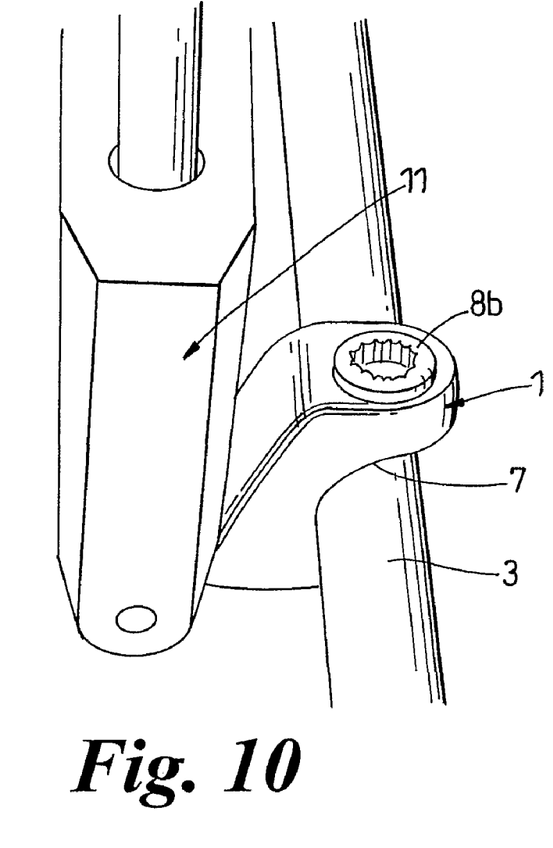

In this position, the instrument 11 and attached connector 1 is lowered into a prepared patient and the clamping hook 6 of the connector 1, which is projecting from the instrument 11 is located around a support rod 3 that has already had at least one end already fastened to a spinal vertebra. In order to hold the instrument 11 steady in this position, the clamping bracket 19 can be secured to an appropriate clamp stand (not shown). Once the support rod 3 has been located in the bight 7 of the connector 1 (see FIG. 9), the locking means 23 is loosened slightly but only to the extent that the bolt 25 disengages from the socket 15, the lug 22 of the guide 21 remaining in position overlying the end of the connector 1. Disengagement of the bolt 25 from the socket 16 allows the connector 1 to rotate around the spigot 13 and this manoeuvre is now carried out so that the connector 1 swivels through 90°, from a first position as shown in FIG. 9, into a second position as shown in FIG. 10. It will be appreciated that the connector 1 pivots about the spigot 13 but also rotates around the support rod 3 so that the clamping hook 6 engages beneath the latter, the connector 1 thus being located in an appropriate position, which may be either an anterior or a posterior position. Once the connector is in this second position, the bolt 25 is again lowered by turning the knob 27 in the opposite direction so that the bolt 25 now engages in the socket 16. The longitudinal axis A1 of the bore 9 is now aligned with longitudinal axis A2 of the tube 18 of the instrument and the awl 30 can be inserted down the tube 18 and through the bore 9 in order that a keyway can be made in the underlying vertebra 10 in preparation for the fastening of a bone anchor 5 thereto. It will be appreciated that the diameter of the tube 18 of the holder 17 is equal to or larger than the diameter of the bone anchor 5 and once the awl 30 has been used, a bone anchor 5 can be inserted down the tube 11 followed by the screwdriver 29 and thereby screwed to the bone 10. Screwdriver 29 is then withdrawn from the tube 11.

Once the bone screw 5 has been fastened to the vertebra 10, the instrument 11 can be disconnected from the connector 1. This is carried out by turning the knob 27 fully, firstly to disengage the bolt 25 from the socket 16 and secondly to retract the lug 22 so that it no longer overlies the end of the connector 1. This then permits the instrument 11 to be disengaged from the connector 1 by withdrawal of the spigot 13 from the pivot socket 12 leaving the connector 1 secured to the underlying vertebra 10 and to the support rod 3, as shown in FIG. 11. The setscrew 8b of the clamping hook 6 can then be appropriately tightened. FIG. 11 also shows the support rod 3 secured to a bone screw 33 that has previously been secured to an adjacent vertebra.

Figure 12:
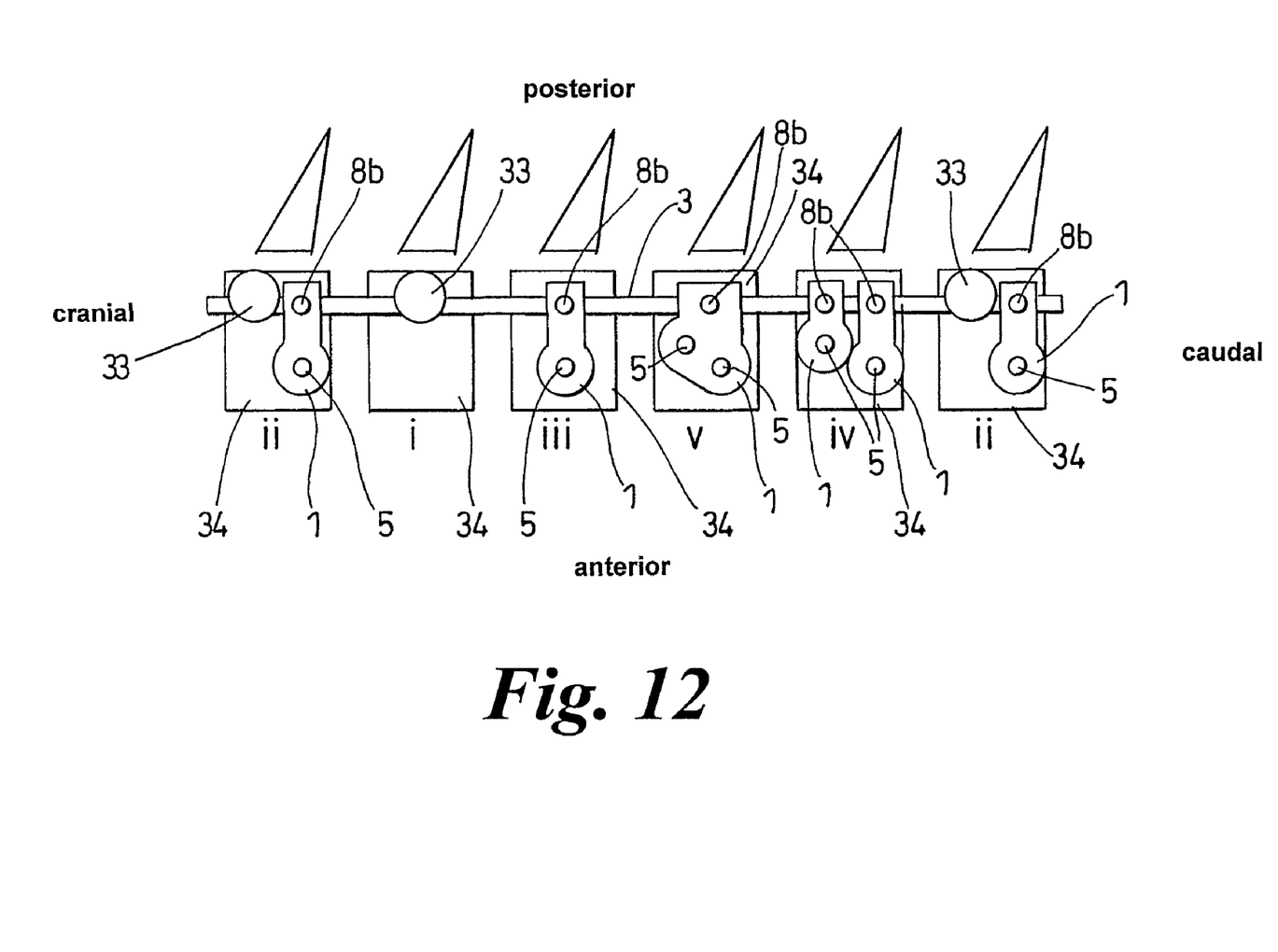
FIG. 12 is a schematic diagram showing modes of use of one or more rod connectors in accordance with the first aspect of the invention.

It will be appreciated that the rod connector 1 can be used in a variety of ways. FIG. 12 shows schematically five modes of use of several rod connectors 1 connected to a support rod 3 that is secured between anterior bone screws 33 and that spans six vertebrae 34 depicted diagrammatically with their posterior side uppermost, their anterior side lowermost, their cranial side to the left and their caudal side to the right with respect to the page. The vertebra labeled i shows one of the bone screws 33 used without any additional stabilization. The two vertebrae labeled ii both show anterior bone screws 33 with connectors 1 used to provide additional stabilization. The vertebra iii is secured to a connector 1 used autarchically as a single implant. Similarly, vertebra iv is secured to two differently sized connectors 1 which are also used autarchically. Finally, vertebra v shows the autarchic use of a modified form of connector 1 which is provided with two bores that each accommodate a bone screw 5. In such a connector one of the screws 5 is secured in a manner similar to that described above and the second screw 5 is then secured to the vertebra thereafter once the instrument 11 has been withdrawn.

Figure 13:
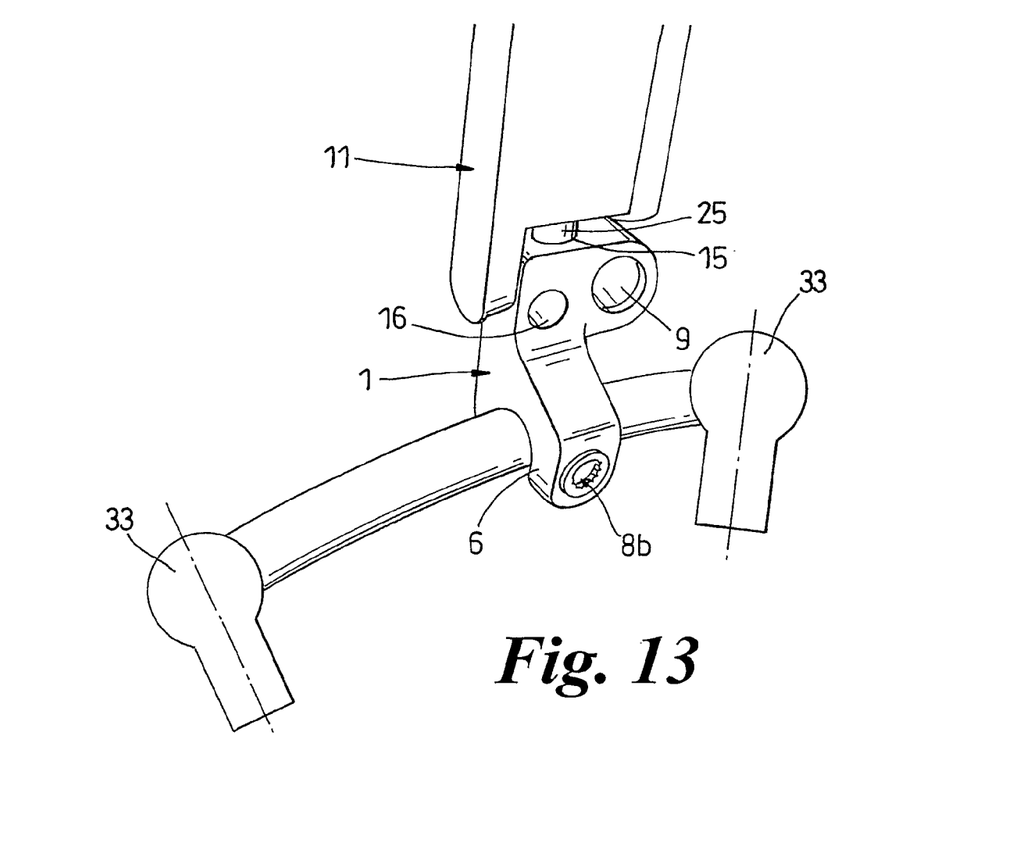
FIGS. 13 to 15 is a sequence showing an operative part of an assembly in use as an instrument in accordance with the third aspect of the invention for the intra-operative rotation of a support rod.
Figure 14:
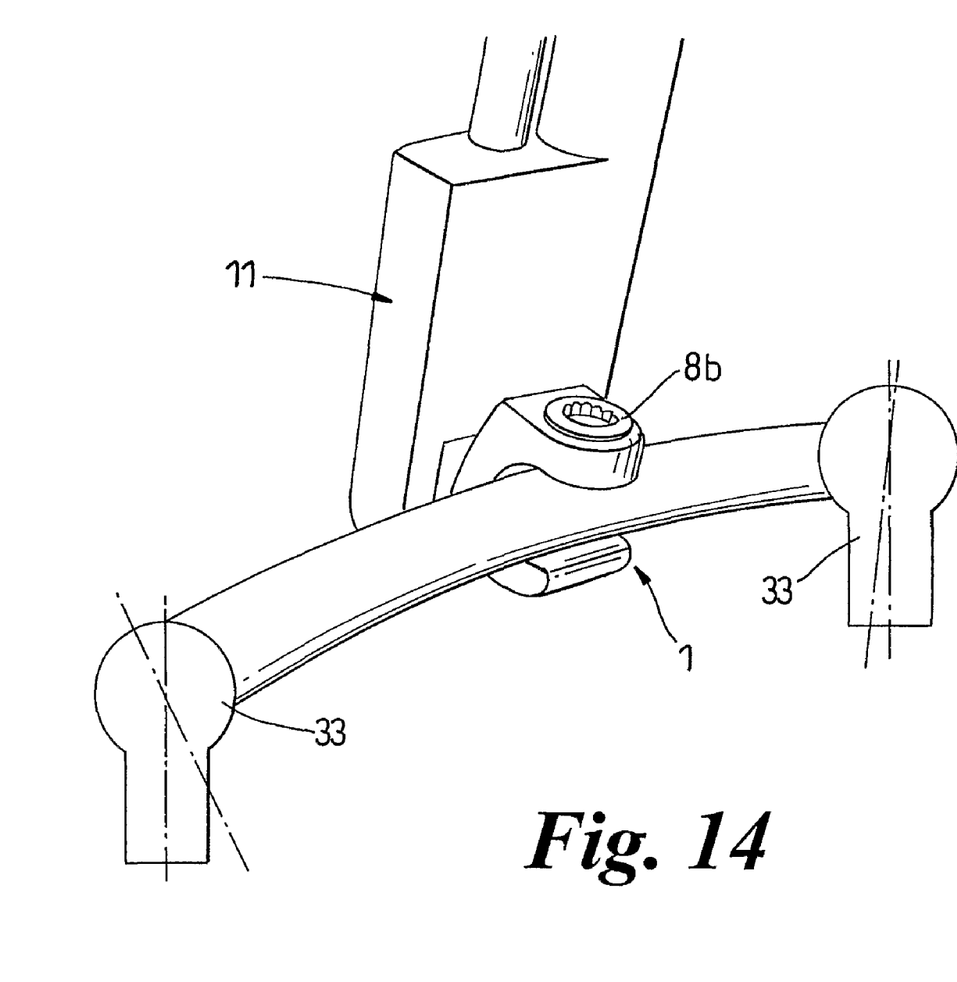
Figure 15:
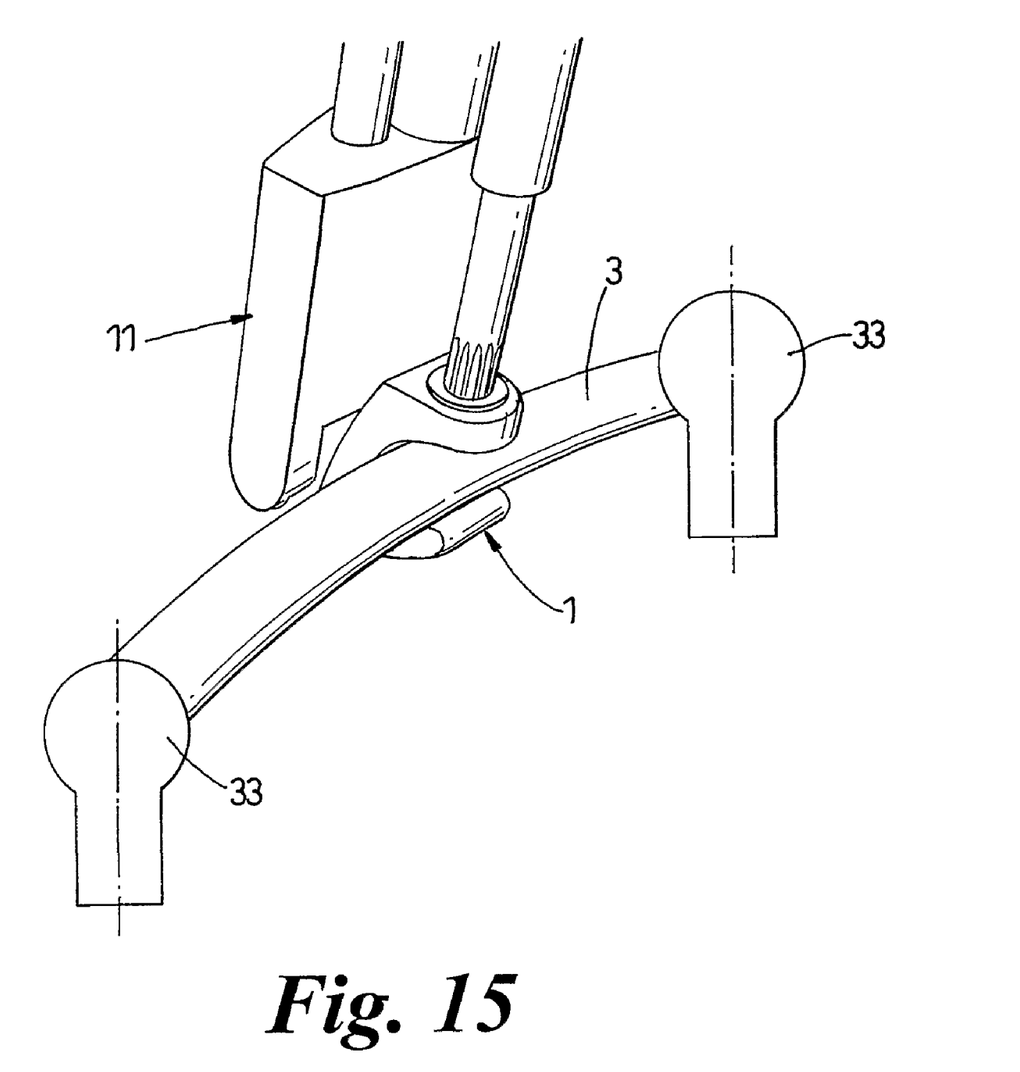

The combination of the instrument 11 and the connector 1 can also be used as a surgical instrument in its own right for intraoperative rod insertion into a patient via a port or a minimal open access surgical incision. FIGS. 13 to 15 is a sequence of drawings showing the use of such a combination. In FIG. 13 a rod connector 1 is secured to an instrument 11 by the pivot means 12, 13 and by engagement of the bolt 25 of the locking means 23 in the socket 15. The connector 1 is thereby retained in its first position. A support rod 3 is secured within the clamping hook 6 via its setscrew 8b. The support rod 3 is then inserted into the patient and secured to pre-positioned bone screws 33 (shown diagrammatically in FIGS. 13 to 15). The end bolt 25 is then retracted from the socket 16 by turning the knob 27 and by pushing the instrument 11 down, the rod 3 is forced to rotate. The rod 3 rotates through 90° in total and this also forces the axes of the anterior bone screws 33 to align, as shown in FIG. 14. Finally, the setscrew 8b is loosened to release the rod 3 from the clamping hook 6. The combination of the instrument 11 and the connector 1 can then be removed from the patient leaving the support rod 3 in place.

Hence, the rod connector 1 and its combination with what in this case comprises an insertion instrument 11 for the connector 1 enables the connector 1 to be used to stabilize spinal instabilities by either a 'single rod, single screw' system or a 'single rod, double screw' system in an manner that is easy to handle and that requires only a minimal surgical opening. In addition, the invention allows the rod connector 1 to be added on to existing single rod systems using an endoscopic approach and to be used in combination with the instrument 11 as an instrument in its own right to manipulate the location and orientation of a spinal support rod. The rod connector is also suitable for use as an anterior rod connector or as a posterior rod connector.

The invention claimed is:

1. A surgical system comprising:
an insertion instrument including a proximal end, a distal end, and a cannulated bore extending from the proximal end to the distal end, the cannulated bore having a longitudinal axis, the insertion instrument further including a projection adjacent to the distal end and a pin moveable associated with the insertion instrument; and
a connector, the connector being sized and configured to connect a bone anchor to a support rod, the connector including:
a channel for receiving the support rod;
a bore for receiving at least a portion of the bone anchor, the bore including a longitudinal axis;
a recess having a longitudinal axis, the recess receiving the projection formed on the insertion instrument so that, once engaged, the connector is pivotably mounted to the insertion instrument between a first position and a second position, wherein when in the first position, the longitudinal axis of the cannulated bore is not aligned with the longitudinal axis of the bore formed in the connector and, when in the second position, the longitudinal axis of the cannulated bore is aligned with the longitudinal axis of the bore formed in the connector; and first and second sockets, the first and second sockets each having a longitudinal axis, the pin being at least partially received within the first socket to couple the connector to the insertion instrument when the connector is in the first position and being at least partially received within the second socket to couple the connector to the insertion instrument when the connector is in the second position.

2. The surgical system of claim 1, wherein the longitudinal axis of the first socket is substantially perpendicular to the longitudinal axis of the second socket.

3. The surgical system of claim 2, wherein the longitudinal axis of the second socket is substantially parallel to the longitudinal axis of the bore formed in the connector.

4. The surgical system of claim 3, wherein the longitudinal axes of the first and second sockets intersect at a point coincident with the longitudinal axis of the recess.

5. The surgical system of claim 4, wherein the longitudinal axis of the bore formed in the connector is angled at an acute angle with respect to a plane coincident with the longitudinal axis of the recess.

6. The surgical system of claim 5, wherein the acute angle is about 7 degrees.

7. The surgical system of claim 1, wherein the insertion instrument further comprises a guide moveably associated with the insertion instrument between an active position and a retracted position wherein, when in the active position, the guide is sized and configured to retain the connector in the first and second positions and, when in the retracted position, the connector can be disengaged from the insertion instrument.

8. The surgical system of claim 7, wherein the guide comprises a sleeve having a projecting lug.

9. The surgical system of claim 7, wherein the guide is operatively coupled to the pin so that movement of the pin with respect to the insertion instrument results in the guide moving with respect to the insertion instrument.

10. The surgical system of claim 1, wherein, when in the first position, the connector is sized and configured so that the support rod can be inserted into the channel formed in the connector, the connector then being rotated about the longitudinal axis of the recess into the second position so that the bone anchor can be inserted through the cannulated bore, at least partially through the bore formed in the connector and into a patient's bone.

11. The surgical system of claim 1, wherein the channel includes a clamping hook with a bight for receiving the support rod and a bore for receiving a setscrew for releasably clamping the support rod located within the bight.

12. A method of coupling a bone anchor to a support rod, the method comprising the steps of:

providing a connector having a channel for receiving the support rod, a bore for receiving at least a portion of the bone anchor, the bore including a longitudinal axis, the connector further including a recess having a longitudinal axis, and first and second sockets;

providing an insertion instrument including a proximal end, a distal end, and a cannulated bore extending from the proximal end to the distal end, the cannulated bore having a longitudinal axis, the insertion instrument further including a projection and a pin moveably associated with respect to the insertion instrument;

coupling the connector to the insertion instrument by inserting the projection of the instrument into the recess of the connector;

moving the pin into engagement with the first socket formed in the connector to retain the connector in a first position relative to the insertion instrument;

inserting the support rod into the channel formed in the connector, wherein the support rod was previously implanted within a patient's body;

moving the pin sufficiently to enable the connector to rotate about the projection;

rotating the connector relative to the insertion instrument from the first position to a second position;

moving the pin into engagement with the second socket formed in the connector to retain the connector in the second position;

securing the connector to a bone of the patient using a bone anchor inserted through the cannulated bore formed in the insertion instrument and at least partially through the first bore formed in the connector; and disengaging the insertion instrument from the connector.

* * * * *